United States Patent
Lynn (10) Patent No.: US 10,232,071 B2
(45) Date of Patent: *Mar. 19, 2019

(54) SYSTEM FOR CREATING AN OXIDATION REDUCTION POTENTIAL (ORP) FOR PATHOGENIC CONTROL, AND FOR PROVIDING WATER-OZONE SOLUTIONS TO A WALL WASHING SYSTEM

(71) Applicant: Daniel W. Lynn, Omaha, NE (US)

(72) Inventor: Daniel W. Lynn, Omaha, NE (US)

( * ) Notice: Subject to any disclaimer, the term of this patent is extended or adjusted under 35 U.S.C. 154(b) by 38 days.

This patent is subject to a terminal disclaimer.

(21) Appl. No.: 15/446,362

(22) Filed: Mar. 1, 2017

(65) Prior Publication Data

US 2017/0202989 A1 Jul. 20, 2017

Related U.S. Application Data (63) Continuation-in-part of application No. 15/355,884, filed on Nov. 18, 2016, which is a
(Continued)

(51) Int. Cl.
| | | |
|---|---|---|
| *C02F 1/00* | (2006.01) | |
| *A61L 2/18* | (2006.01) | |
| *C02F 1/78* | (2006.01) | |
| *B01F 5/04* | (2006.01) | |
| *B01F 3/04* | (2006.01) | |
| *B09C 1/00* | (2006.01) | |
| *B01D 29/00* | (2006.01) | |

(Continued)

(52) U.S. Cl.
CPC ........... *A61L 2/183* (2013.01); *B01F 3/04503* (2013.01); *B01F 5/0413* (2013.01); *C02F 1/78* (2013.01); *A61L 2202/11* (2013.01); *B01F 2003/04886* (2013.01); *C02F 2201/782* (2013.01); *C02F 2209/001* (2013.01); *C02F 2209/04* (2013.01); *C02F 2209/40* (2013.01)

(58) Field of Classification Search
CPC .. A01C 1/04; A61M 1/16; A61L 2/183; A61L 2201/04886; B01D 17/0217; B01D 21/305; B01D 29/00; B09C 1/00; B01F 3/04503; B01F 5/04; B01F 5/0413; B01F 5/0428; B01F 2003/04886
USPC ...... 210/85, 87, 90, 96.1, 97, 136, 137, 150, 210/151, 192, 202, 259, 607, 61, 4, 631, 210/724, 739, 741, 743, 746, 750, 760, 210/769
See application file for complete search history.

(56) References Cited

U.S. PATENT DOCUMENTS 3,719,327 A * 3/1973 McMahan ............ A01G 25/023
239/454
5,248,218 A * 9/1993 Belcher ................... F16L 45/00
138/37

(Continued)

*Primary Examiner* — Hayden Brewster
(74) *Attorney, Agent, or Firm* — Dennis L. Thomte; Thomte Patent Law Office LLC (57) ABSTRACT

Systems and methods for creating an oxidation reduction potential (ORP) in water for pathogenic control are described. The systems and methods generate an oxidation reduction potential that provides pathogenic control of the solution as well as pathogenic control of the surfaces with which the solution comes in immediate contact. The system is designed to disinfect and cleanse at least one wall by discharging the water/ozone solution onto the wall at the upper end thereof.

15 Claims, 10 Drawing Sheets

Related U.S. Application Data continuation-in-part of application No. 15/050,777, filed on Feb. 23, 2016.

(60) Provisional application No. 62/121,770, filed on Feb. 27, 2015.

(51) Int. Cl.
*B01D 46/00* (2006.01)
*C05F 7/00* (2006.01)
*C05F 9/00* (2006.01)

(56) References Cited

U.S. PATENT DOCUMENTS

| | | |
|---|---|---|
| 6,153,105 A | 11/2000 | Tadlock et al. |
| 6,334,328 B1 | 1/2002 | Brill |
| 6,685,825 B1 | 2/2004 | Chang |
| 8,071,526 B2 | 12/2011 | Lynn |
| 8,075,705 B2 | 12/2011 | Lynn |
| 9,068,149 B2 | 6/2015 | Lynn |
| 9,151,528 B2 | 10/2015 | Erbs et al. |
| 9,174,845 B2 | 11/2015 | Lynn |
| 9,522,348 B2 | 12/2016 | Lynn |
| 2004/0004042 A1 | 1/2004 | Hadley et al. |
| 2004/0168989 A1 | 9/2004 | Tempest, Jr. |
| 2009/0142225 A1 | 6/2009 | Tornqvist |
| 2010/0219137 A1 | 9/2010 | Lacasse |
| 2013/0193081 A1 | 8/2013 | Vasiliu et al. |
| 2014/0027388 A1* | 1/2014 | Constant .................. C02F 1/78 210/760 |
| 2014/0263097 A1 | 9/2014 | Lynn |
| 2016/0251243 A1 | 9/2016 | Lynn |

* cited by examiner

SYSTEM FOR CREATING AN OXIDATION REDUCTION POTENTIAL (ORP) FOR PATHOGENIC CONTROL, AND FOR PROVIDING WATER-OZONE SOLUTIONS TO A WALL WASHING SYSTEM

CROSS-REFERENCE TO RELATED APPLICATIONS

The application is a Continuation-in-Part Application of U.S. application Ser. No. 15/355,884 filed Nov. 18, 2016 entitled SYSTEMS AND METHODS FOR CREATING AN OXIDATION REDUCTION POTENTIAL (ORP) IN WATER FOR PATHOGENIC CONTROL which is a Continuation-in-Part of U.S. application Ser. No. 15/050,777 filed Feb. 23, 2016 entitled SYSTEMS AND METHODS FOR CREATING AN OXIDATION REDUCTION POTENTIAL (ORP) IN WATER FOR PATHOGENIC CONTROL which claims the benefit of U.S. Provisional Application Ser. No. 62/121,770 entitled SYSTEMS AND METHODS FOR CREATING AN OXIDATION REDUCTION POTENTIAL (ORP) IN WATER FOR PATHOGENIC CONTROL, all of which are hereby incorporated by reference thereto to complete this disclosure if necessary.

BACKGROUND OF THE INVENTION

Field of the Invention

This invention relates to improved systems and methods for creating an oxidation reduction potential (ORP) in water for pathogenic control and to provide the water and ozone solution thereof to a wall washing system.

Description of the Related Art

Water intended for potable use (e.g., drinking water), may contain disease-causing organisms, or pathogens, which can originate from the source of the water, from resistance to water treatment techniques, from improper or ineffectual water treatment techniques, or so forth. Pathogens include various types of bacteria, viruses, protozoan parasites, and other organisms. To protect drinking water from disease-causing organisms, or pathogens, water suppliers often add a disinfectant, such as chlorine, to the water. However, disinfection practices can be ineffectual because certain microbial pathogens, such as *Cryptosporidium*, are highly resistant to traditional disinfection practices. Also, disinfectants themselves can react with naturally-occurring materials in the water to form byproducts, such as trihalomethanes and haloacetic acids, which may pose health risks.

A major challenge for water suppliers is how to control and limit the risks from pathogens and disinfection byproducts. It is important to provide protection from pathogens while simultaneously minimizing health risks to the population from disinfection byproducts. Oxidation reduction potential (ORP) can be used for water system monitoring to reflect the antimicrobial potential of the water, without regard to the water quality, with the benefit of a single-value measure of the disinfection potential, showing the activity of the disinfectant rather than the applied dose.

In installations wherein vegetables, fruit, et. al., are treated (with chlorine or other materials), it is necessary to spray the walls of the area to remove chlorine, organic particles, etc., from the walls of the area to cleanse and disinfect the same. The usual method of cleansing and disinfecting the walls of the area is to simply use a water hose to spray water or a water-chlorine mixture onto the walls of the area. Such is a time-consuming task and results in areas other than the walls of the area being sprayed.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

Systems and methods for creating an oxidation reduction potential (ORP) in water for pathogenic control are described. A system embodiment includes an ozone generator, a water inlet, a venturi, and a water outlet. The venturi is positioned to receive ozone generated by the ozone generator and to receive water from the water inlet, where the venturi provides mixing of the water and ozone to provide a water and ozone solution having an ORP suitable for pathogenic control.

The instant invention relates to an improved means for cleansing and disinfecting the walls of an area wherein food, fruit or vegetables are being handled.

It is a principal object of the invention to provide improved systems and methods for creating an oxidation reduction potential (ORP) in water for the pathogenic control spraying of the walls of an enclosure or areas with the water-ozone solution.

A further object of the invention is to entirely replace the use of chlorine in all the processes performed within a facility such as fruit and vegetable handling facilities.

A further object of the invention is to provide a system designed to reduce the effects of the environmental damages caused by the corrosive properties of chlorine or other toxic materials on the floors, walls and equipment within a facility such as fruit and vegetable handling facilities.

A further object of the invention is to provide a system wherein the water and ozone solution produced by the system will not harm persons coming into contact with the water and ozone solution of this invention.

Still another object of the invention is to provide a water and ozone solution which is a FDA approved antimicrobial agent and which has FDA approval for contact with food or as a food additive.

These and other objects will be apparent to those skilled in the art.

BRIEF DESCRIPTION OF THE DRAWINGS

The detailed description is described with reference to the accompanying figures. In the figures, the use of the same reference numbers in different instances in the description and the figures may indicate similar or identical items.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

An Oxidation reduction potential (ORP) value can be used for water system monitoring to reflect the antimicrobial potential of a given sample of water. ORP is measured in millivolts (mV), with typically no correction for solution temperature, where a positive voltage shows a solution attracting electrons (e.g., an oxidizing agent). For instance, chlorinated water will show a positive ORP value whereas sodium sulfite (a reducing agent) loses electrons and will show a negative ORP value. Similar to pH, ORP is not a measurement of concentration directly, but rather of activity level. In a solution of only one active component, ORP indicates concentration. The World Health Organization (WHO) adopted an ORP standard for drinking water disinfection of 650 millivolts. That is, the WHO stated that when the oxidation-reduction potential in a body of water measures 650 (about ⅔ of a volt), the sanitizer in the water is active enough to destroy harmful organisms almost instantaneously. For example E. coli, Salmonella, Listeria, and Staph pathogens have survival times of under 30 seconds when the ORP is above 650 mV, compared against >300 seconds when it is below 485 mV.

An example ORP sensor uses a small platinum surface to accumulate charge without reacting chemically. That charge is measured relative to the solution, so the solution "ground" voltage comes from the reference junction. For example, an ORP probe can be considered a millivolt meter, measuring the voltage across a circuit formed by a reference electrode constructed of silver wire (in effect, the negative pole of the circuit), and a measuring electrode constructed of a platinum band (the positive pole), with the water in-between.

Increasingly, microbial issues are commanding the attention of water treatment operators, regulators, media, and consumers. There are many treatment options to eliminate pathogenic microbes from drinking water. One such option includes ozone ($O_3$), an oxidizing agent approved for drinking water treatment by the U.S. Environmental Protection Agency. For instance, ozone is one of the strongest disinfectants approved for potable water treatment capable of inactivating bacteria, viruses, Giardia, and Cryptosporidium.

Accordingly, the present disclosure is directed to systems and methods for creating an oxidation reduction potential (ORP) in water for pathogenic control. An example system includes an ozone generator, a water inlet, a water outlet, and a venturi (e.g., a Venturi tube, venturi injector, etc.) coupled with each of the ozone generator, the water inlet, and the water outlet. Such example system is configured to output water having an ORP of about 600 mV to about 800 mV, with particular implementations being configured to output water having an ORP of about 650 mV to about 750 mV to provide pathogenic control.

Example Implementations

Figure 1:
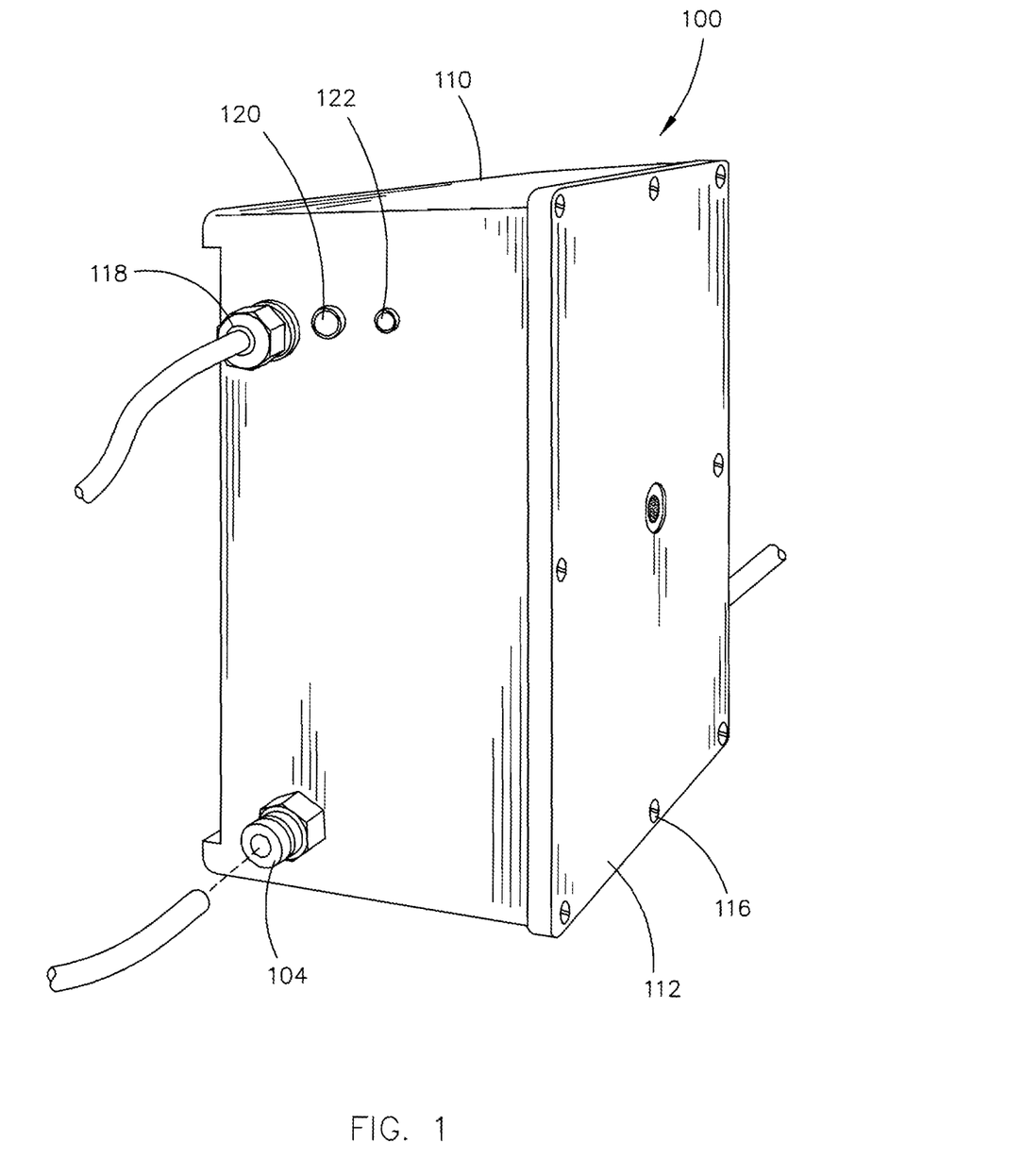
FIG. 1 is a perspective view of a system for creating an oxidation reduction potential (ORP) in water for pathogenic control in accordance with example implementations of the present disclosure.
Figure 2:
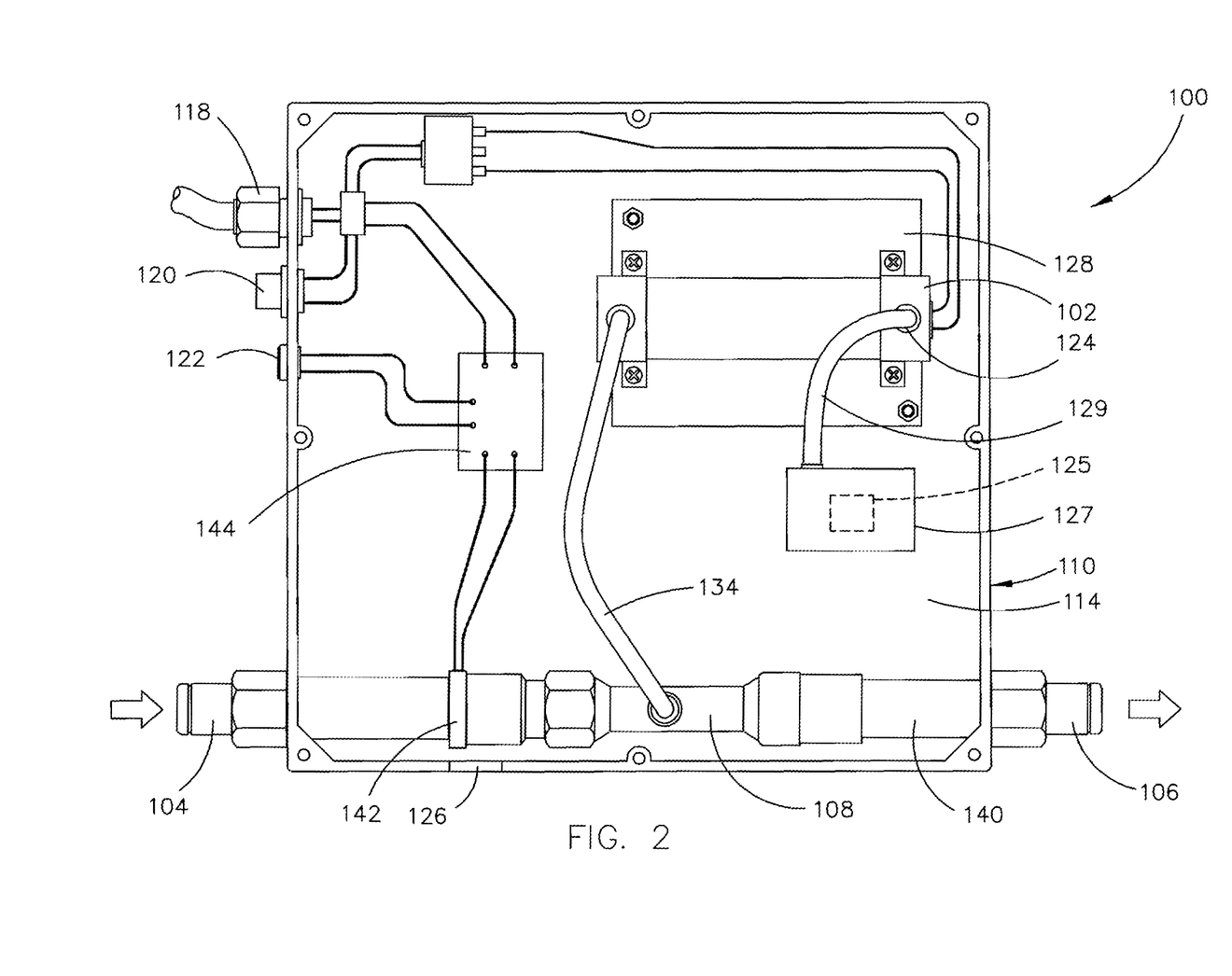
FIG. 2 is a top view of a system for creating an oxidation reduction potential (ORP) in water for pathogenic control in accordance with example implementations of the present disclosure.
Figure 3:
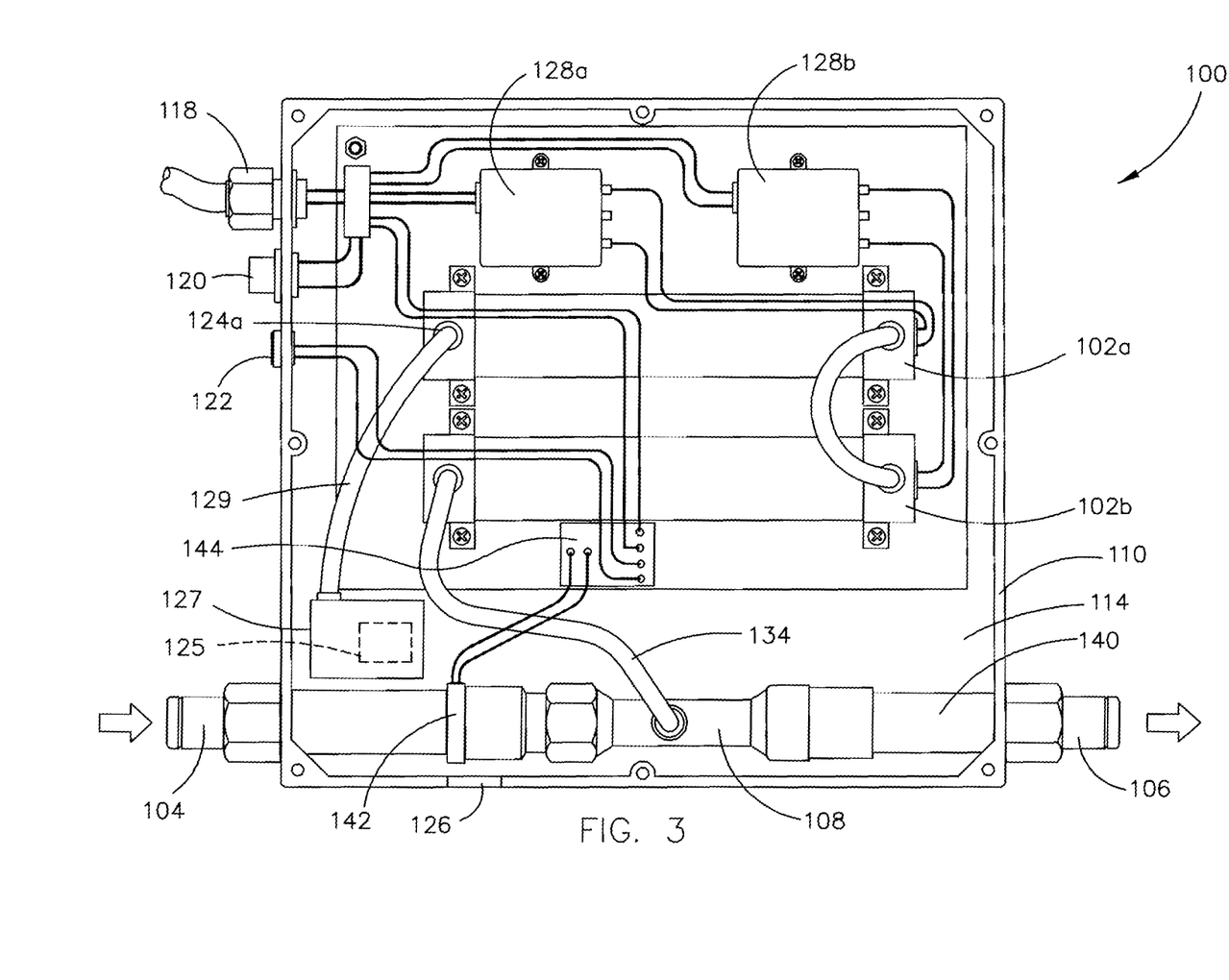
FIG. 3 is a top view of a system for creating an oxidation reduction potential (ORP) in water for pathogenic control in accordance with example implementations of the present disclosure.

Referring generally to FIGS. 1-3, a system 100 for creating an oxidation reduction potential (ORP) in water for pathogenic control is shown in accordance with example implementations of the present disclosure. As shown, the system 100 generally includes an ozone generator 102, a water inlet 104, a water outlet 106, and a venturi 108 (e.g., a Venturi tube, venturi injector, etc.) coupled with each of the ozone generator 102, the water inlet 104, and the water outlet 106. The system 100 can include a housing 110 for receiving the water inlet 104 and the water outlet 106 and the venturi 108 there-between and for mounting the ozone generator 102. The housing 110 can include a removable cover portion 112 which can enclose (e.g., when secured) and provide access to (e.g., when removed) the components housed in an interior portion 114 of the housing 110. The removable cover portion 114 can be secured to the housing 110 via one or more fasteners 116 (e.g., screws to mate with bores in the housing 110). The housing 110 can further include coupling portions to couple with a power source 118, a switch 120 to engage or disengage power to the system 100, an indicator 122 (e.g., a light source), and the like.

In implementations, the conventional ozone generator 102 includes a corona discharge tube configured to use oxygen from the surrounding air to generate ozone, such as through splitting of oxygen molecules in the air through electrical discharge caused by supplying power to a dielectric material within the corona discharge tube. For example, the ozone generator 102 can include an input port 124 to receive ambient air within the housing 110 into the ozone generator 102 to convert oxygen from the ambient air into ozone. The housing 110 can include an aperture 126 to receive ambient air into the housing 110, such as when the removable cover portion 112 is secured in place. In implementations, the power source 118 can include a 120V power supply that is transformed via transformer 128 suitable for applying the voltage to the dielectric within the corona discharge tube of the ozone generator 102. For example, the ozone generator 102 can be operated at 110 volts/60 Hz and have an operating frequency of about 450 KHz and 550 KHz, with a power rating of less than about 15 watts, and with a unit performance for electrical consumption of about 32 watts. In implementations, the ozone generator 102 has an operating frequency of about 480 KHz. Further, the ozone generator 102 can be provided according to ISO 9001 CE standards. The ozone generator 102 can produce from about 800 mg ozone per hour to about 1200 mg ozone per hour. In implementations, the ozone generator 102 produces about 1000 mg ozone per hour. The ozone generator 102 can include other methods and systems for generating ozone, including but not limited to, electrochemical cells configured to generate ozone from water by placing an anode and a cathode in contact with opposite sides of a proton exchange membrane (PEM), and supplying power to the cell, whereby water flowing over the surface of the anode breaks down into hydrogen atoms and oxygen atoms that assemble to form $O_3$ (ozone).

The system 100 can include one or more of a filter 125 (or dryer) and a compressor 127 in communication with the input port 124 via a coupling 129 to filter and/or compress ambient air received by the ozone generator 102. For example, the compressor 127 can include a port to receive ambient air (e.g., air within the interior region 114 of the housing 110), whereby the filter 125 interacts with the air, which is then introduced to the ozone generator 102 via the coupling 129 and the input port 124. The filter 125 can dry the air received by the compressor 127 by removing water vapor or moisture therefrom, where the water could inhibit the production of ozone by the ozone generator 102. The pressure provided by the compressor 127 can vary depending on the water pressure supplied to the system 100 via the water inlet 104, where the pressure applied by the compressor 127 can be balanced based on the flow rate of air received by the ozone generator 102 via the input port 124 and the water pressure supplied to the system 100 via the water inlet 104 to obtain a particular ORP of the water at the water outlet 106. For example, in implementations, the compressor 127 can compress the filtered air at least about 15 KPa (e.g., more particularly at a pressure of 18 KPa or about 2.6 psi) to provide a gas throughput in the ozone generator 102 of about 8 SCFH (standard cubic feet per hour), where the water pressure at the water inlet 104 is about 50 psi to 55 psi (e.g., a reasonable rating for many residential and commercial facilities), to provide an ORP in the water at the water outlet of at least about 600 mV (e.g., about 600 mV to about 800 mV, more particularly about 650 mV to about 750 mV). At these pressures, the ozone generator 102 has a residence time of the gas of about three seconds. The pressure applied by the compressor 127 of the ozone generator 102 can affect the rate at which the gas flows through the ozone generator 102, which can affect contact time of the air with the components of the ozone generator 102, which can also affect mass gas transfer rates within the ozone generator 102.

In implementations, the system 100 can include a plurality of ozone generators 102. For example, as shown in FIG. 3, the system 100 includes a first ozone generator 102a and a second ozone generator 102b in series with the first ozone generator 102a. The first ozone generator 102a is supplied with power from a first transformer 128a coupled with the power source 118, whereas the second ozone generator 102b is supplied with power from a second transformer 128b also coupled with the power source 118. Ambient air from within the housing 110 can be drawn into the first ozone generator 102a via the port 124a (where such air can be filtered and compressed), where fluids can be subsequently introduced to the second ozone generator 102b in series with the first ozone generator 102a via coupling 130. In implementations, the plurality of ozone generators 102 provides one or more backup ozone generators 102 in case of malfunction or inoperability of one or more of the other ozone generators 102. Each ozone generator 102 can include an operating life of about 10,000 working hours.

Figure 4:
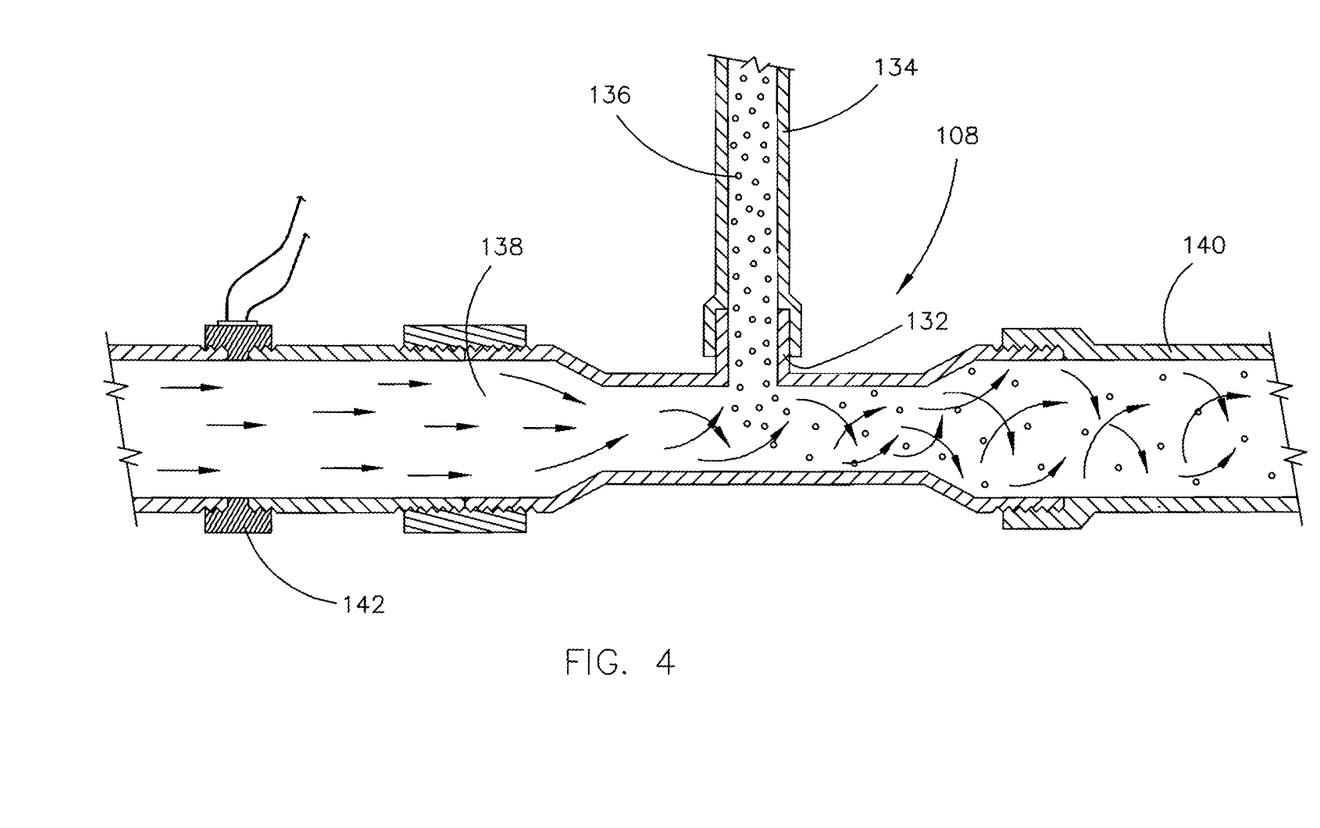
FIG. 4 is a partial cross-sectional view of a flow control portion of a system for creating an oxidation reduction potential (ORP) in water for pathogenic control, such as the system shown in FIG. 2 or 3.
Figure 5:
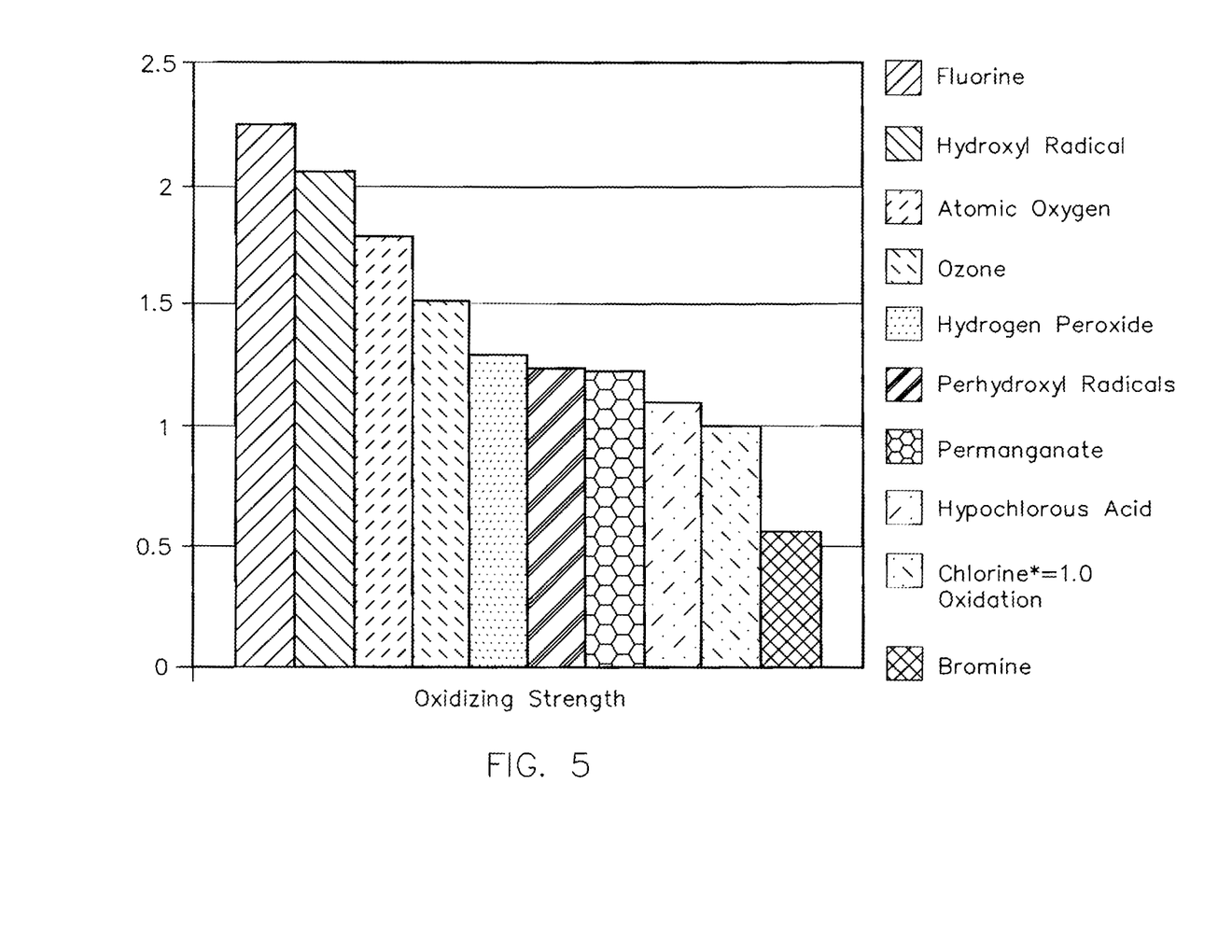
FIG. 5 is a chart of relative oxidation strength of certain oxidizers.

Referring to FIGS. 2-4, the venturi 108 can include an injector venturi design (e.g., a "T" design), where the venturi 108 is coupled between the water inlet 104 and the water outlet 106, and where ozone generated by the ozone generator 102 is introduced to the venturi 108 through another port (e.g., port 132) positioned perpendicular to the flow path of the water (from the water inlet 104 to the water outlet 106). In implementations, the venturi 108 is coupled to the ozone generator via a coupling 134 connected to port 132. During operation, the ozone generated by the ozone generator 102 is drawn into the venturi 108 and mixed with the water stream flowing from the water inlet 104 to the water outlet 106. A pressure differential between the water inlet 104 and the water outlet 106 is utilized to facilitate drawing the ozone into the venturi 108 and to facilitate mixing of the ozone and the water. FIG. 4 provides a diagrammatic representation of ozone molecules 136 mixing with water 138 (e.g., via vortex action) within the venturi 108, and further mixing downstream from the port 132 toward the water outlet 106. In an implementation, a pressure differential greater than 20 psi inlet over outlet (e.g., at least a 20 psi difference between the water inlet 104 and the water outlet 106, with pressure higher at the water inlet 104) is provided to generate negative suction in the venturi 108 relative to the ozone generator 102 to thereby draw in the generated ozone through the port 132, while assuring the energy for water flow and pressure for operation of the venturi 108.

In implementations, in order to further increase effectiveness of the mixing process delivered by the venturi 108, the water and ozone solution passes through an in-line mixer 140 coupled between the venturi 108 and the water outlet 106. The in-line mixer 140 can facilitate further breaking or mixing of ozone bubbles already introduced to the water to generate a mixture (or solution) of water and substantially uniform-sized ozone bubbles. The small uniform-size ozone bubbles can adhere to each other to lower the surface tension of the water and ozone solution. For example, water can have a surface tension of about 72 Newtons (N), whereas the solution of water and substantially uniform-sized ozone bubbles can have a surface tension of about 58 Newtons (N). In implementations, the in-line mixer 140 has an internal diameter that equals an internal diameter of the output port of the venturi to which the in-line mixer 140 is coupled. The same internal diameter can provide an uninterrupted transition of the fluid flowing from the venturi 108 to the in-line mixer 140, such as to maintain a vortex action or mixing action of the water and the ozone bubbles. The in-line mixer 140 also provides increased contact time between the water and ozone bubbles and can facilitate preparation of uniform ozone bubble size. In implementations, the in-line mixture 140 has a length of about two inches downstream from the venturi 108, which can allow sufficient time for the velocity of the vortex action caused by the pressure differential of the venturi 108 to crush the gaseous bubbles entrained in the solution into uniformed size bubbles. The in-line mixer 140 can also reintroduce undissolved gas back into the solution resulting in increased efficiency as well as reduced off-gas at the point of application. The in-line mixer 140 can include multiple chambers through which the water and ozone solution flows. The size of the chambers can be determined based on the water flow (e.g., throughput), gas mixing, and desired time exposure. In implementations, operation of the system 100 produces a water stream at the water outlet 106 having a molar concentration of ozone of at least 20%, or more particularly at least 25%, far surpassing previous systems that have mass gas transfer rates of less than 10%.

In implementations, the system 100 is an ultra-compact system (e.g., 8"×8"×4" enclosure, 12"×12"×6" enclosure, or the like) configured to provide an ozone-rich water stream at a rate of about 3 gal/min, and can treat water having inlet pressures of between 15 psi and 85 psi to provide water having an ORP of between 650 mV and 750 mV to provide pathogenic control without introduction of harsh treatment chemicals, such as chlorine. After operation of the system 100, the output water/ozone mixture can provide removal of organic and inorganic compounds, can provide removal of micro-pollutants (e.g., pesticides), can provide enhancement of the flocculation/coagulation decantation process, can provide enhanced disinfection while reducing disinfection by-products, can provide odor and taste elimination of the treated water, and so forth. The solubility of ozone in water is quite good, about 10 to 15 times greater than for oxygen under normal drinking water treatment conditions. About 0.1 to 0.6 liters of ozone will dissolve in one liter of water. The size of the ozone gas bubble in the system 100 can influence gas transfer characteristics. In implementations, the venturi 108 and in-line mixer 140 provide an ozone bubble size of about 2 to about 3 microns. For instance, micro-bubbles can be produced via the venturi 108, and/or sheared into uniformed micro-size bubbles as the solution passed through the in-line mixer 140.

Corona discharge ozone can be used virtually anywhere, such as with portable implementations of the system 100. Since ozone is made on site, as needed and where needed, there is no need to ship, store, handle or dispose of it, nor any containers associated with shipping, storing, handling, and disposing a treatment chemical, as is the situation with most chemicals utilized in water treatment.

The system 100 can provide indications pertaining to the operation status of the system 100, such as to ensure proper operation, or to provide an indication regarding a need for adjustment, servicing, or maintenance. For example, with general reference to FIGS. 1-4 in an implementation, the system 100 further includes a flow meter 142 coupled between the water inlet 104 and the water outlet 106. The flow meter 142 is shown coupled between the water inlet 104 and the venturi 108, however in implementations, a flow meter 142 could be additionally or alternatively coupled between the venturi 108 and the water outlet 106. The flow meter 142 can be configured to provide an electric signal indicative of a flow of fluid through the system 100. For example, the flow meter 142 can include a mechanical flow meter, an electromagnetic flow meter, a pressure-based flow meter, an optical flow meter, or the like, configured to provide an electric signal indicative of a flow of fluid (e.g., water) through the system 100. In implementations, the flow meter 142 can include a solenoid-based flow detector, such as to avoid significant restriction of flow between the water inlet 104 and the water outlet 106. The flow meter 142 can be configured to send the signal to the indicator 122 that provides a visual, tactile, or audible indication that the fluid (e.g., water) is flowing through the system 100. In an implementation, the indicator 122 is a light source (e.g., an LED) configured to illuminate upon receiving a signal from the flow meter 142. In an implementation, the indicator 122 is also coupled to a sensor (e.g., a relay) configured to measure that a voltage is applied to the ozone generator 102. When a proper voltage is applied to the ozone generator 102, the sensor can send a signal to the indicator 122. In an implementation, the indicator will provide a visual, tactile, or audible indication when each of the sensor and the flow meter 142 provide their respective signals to the indicator 122. For example, the system 100 can include a relay 144 coupled to each of the power source 118 and the flow meter 142. The relay 144 is configured to send an activation signal to the indicator 122 when the power source 118 is providing power to the ozone generator 102 and when the flow meter 142 provides a signal regarding fluid flow through the system 100. In such a configuration, the indicator 122 can verify that the system 100 is operating under design conditions (e.g., having an active flow of water, and having a sufficient power supply to the ozone generator 102).

The system 100 can be configured to provide multiple options for distribution of the solution of water and ozone provided at the water outlet 106. The system 100 includes a distribution line 148 which extends from water outlet 106. The system 100 also includes a water line 150 which extends from water inlet 104. Water line 150 is connected to water line 152 by a tee-fitting 154. Water line 152 is connected to a source of water under pressure. The distribution line 148 is fluidly connected to the intake side of pump 156. Pump 156 has a water/ozone distribution line 158 extending from the discharge side of pump 156. Line 158 extends outwardly through wall 160 of an enclosure or room for connection to a valve 162. A distribution line 164 extends from valve 162 to an elongated and horizontally disposed spray pipe or conduit 166 which has spray nozzles 168 secured thereto in a spaced-apart manner. Depending upon the configuration of the room or enclosure, the spray pipe or conduit 166 will be positioned at the upper end of the wall 160 or at the upper ends of the walls around the area to be cleansed and disinfected. Any number of the systems 100 may be utilized. When a plurality of systems 100 are utilized, the distribution lines 148 are connected to pump 156 in a parallel manner.

When it is desired to disinfect or cleanse the walls 160, the systems 100 are activated to supply the water/ozone solutions to the pump 156. Pump 156 will be energized to pump the water/ozone solution to each of the pipes 166 so that the water/ozone solution is sprayed onto the upper ends of the walls 160 with the water/ozone solution flowing down the walls 160 to disinfect and cleanse the walls 160.

In implementations, the system 100 can include an in-line ORP meter positioned to measure the ORP of the water and ozone solution, such as adjacent the water outlet (e.g., within the housing 110, outside the housing 110, etc.), coupled with the distribution line 146, or the like. The in-line ORP meter can be coupled with the relay 144, such that the in-line ORP meter provides a signal to the relay 144 upon detection of a desired ORP or range of ORPs (e.g., at least 600 mV, at least 650 mV, etc.). The relay 144 can then provide an activation signal to the indicator 122 upon proper functioning of the system 100 (e.g., when the power source 118 is providing power to the ozone generator 102, when the flow meter 142 provides a signal regarding fluid flow through the system 100, and when the in-line ORP meter detects a desired ORP of the water and ozone solution generated by the system 100). When the indicator 122 is not activated, this can provide an indication that a component or components of the system 100 may need adjustment, servicing, or maintenance. Alternatively, the system 100 can be configured to activate the indicator 122 upon failure of one or more of the components of the system 100 (e.g., no power supplied to the ozone generator 102, no flow of water detected by the flow meter 142, or an undesired ORP detected by the in-line ORP meter).

By providing an ORP of between 650 mV and 750 mV with the system, the output water can be utilized to destroy various pathogens, including, but not limited to, algae (e.g., blue-green), bacteria (e.g., *Aeromonas & Actinomycetes, Bacillus, Campylobacters, Clostridium botulinum, Escherichia coli* (*E. coli*), *Flavobacterium, Helicobacter* (*pylori*), *Heterotrophic Bacteria, Legionella pneumophila, Micrococcus, Mycobacterium tuberculosis, Pseudomonas aeruginosa, Salmonella, Shigella shigellosis* (dysentery), *Staphylococcus* sp, *albus, aureus, Streptococcus, Vibrio: alginolyticus, anguillarium, parahemolyticus, Yersinia*

*enterocolitica*), fungi, molds, yeasts, mold spores, nematodes, protozoa (e.g., *Acanthamoeba & Naegleria, Amoeboe Trophozoites, Cryptosporidium, Cyclospora, Entamobea* (*histolytica*), *Giardia lamblia, Giardia muris, Microsporidium, N. gruberi*), trematodes, viruses (e.g., Adenovirus, Astrovirus, Callcivirus, Echovirus, Encephalomyocarditis, Enterovirus, coxsachie, poliovirus, Hepatitis A, B and C, Myxovirus influenza, Norwalk, Picobirnavirus, Reovirus, Rotavirus).

Water Treatment

Figure 6:
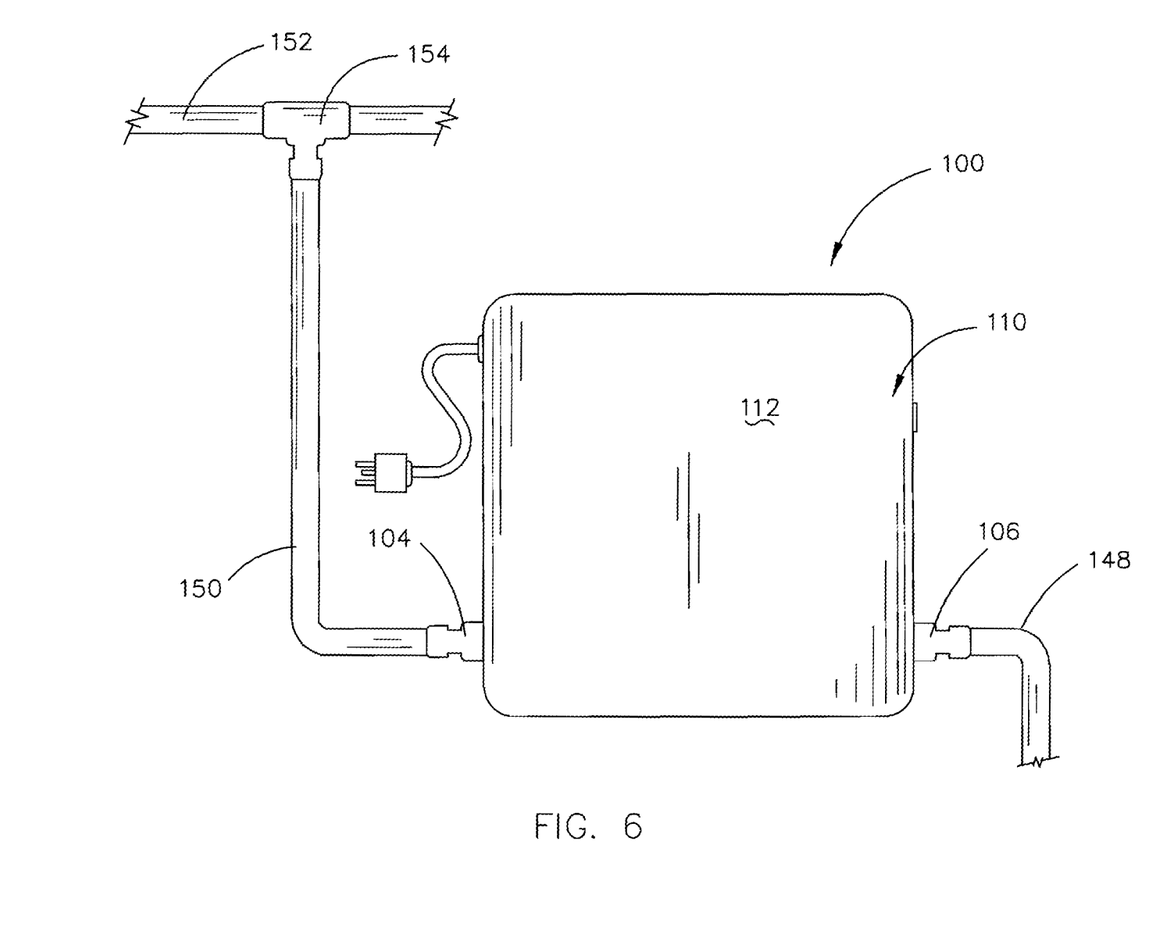
FIG. 6 is a side view of one of the systems of this invention.
Figure 7:
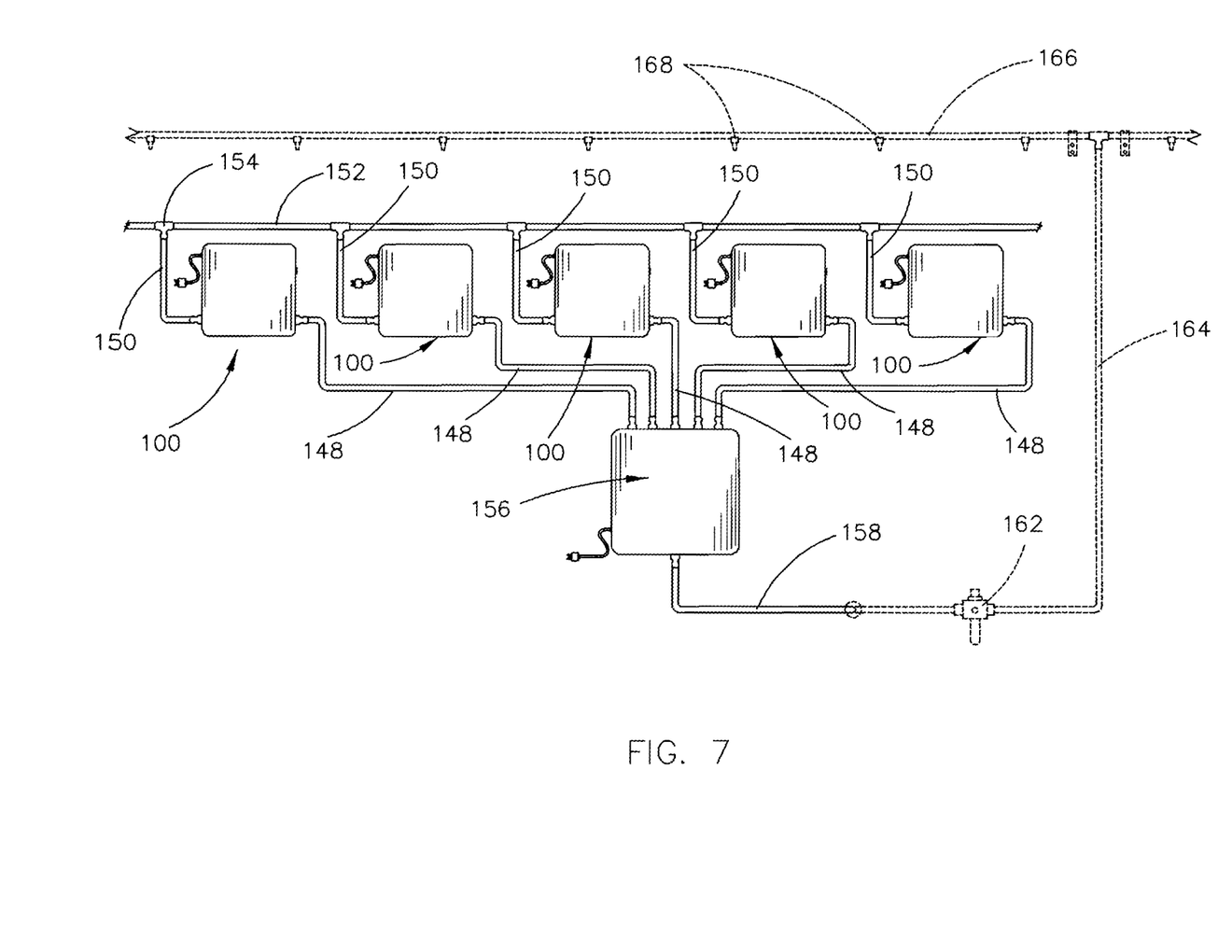
FIG. 7 is a partial schematic of the systems of this invention connected to a wall mounted spray pipe.
Figure 8:
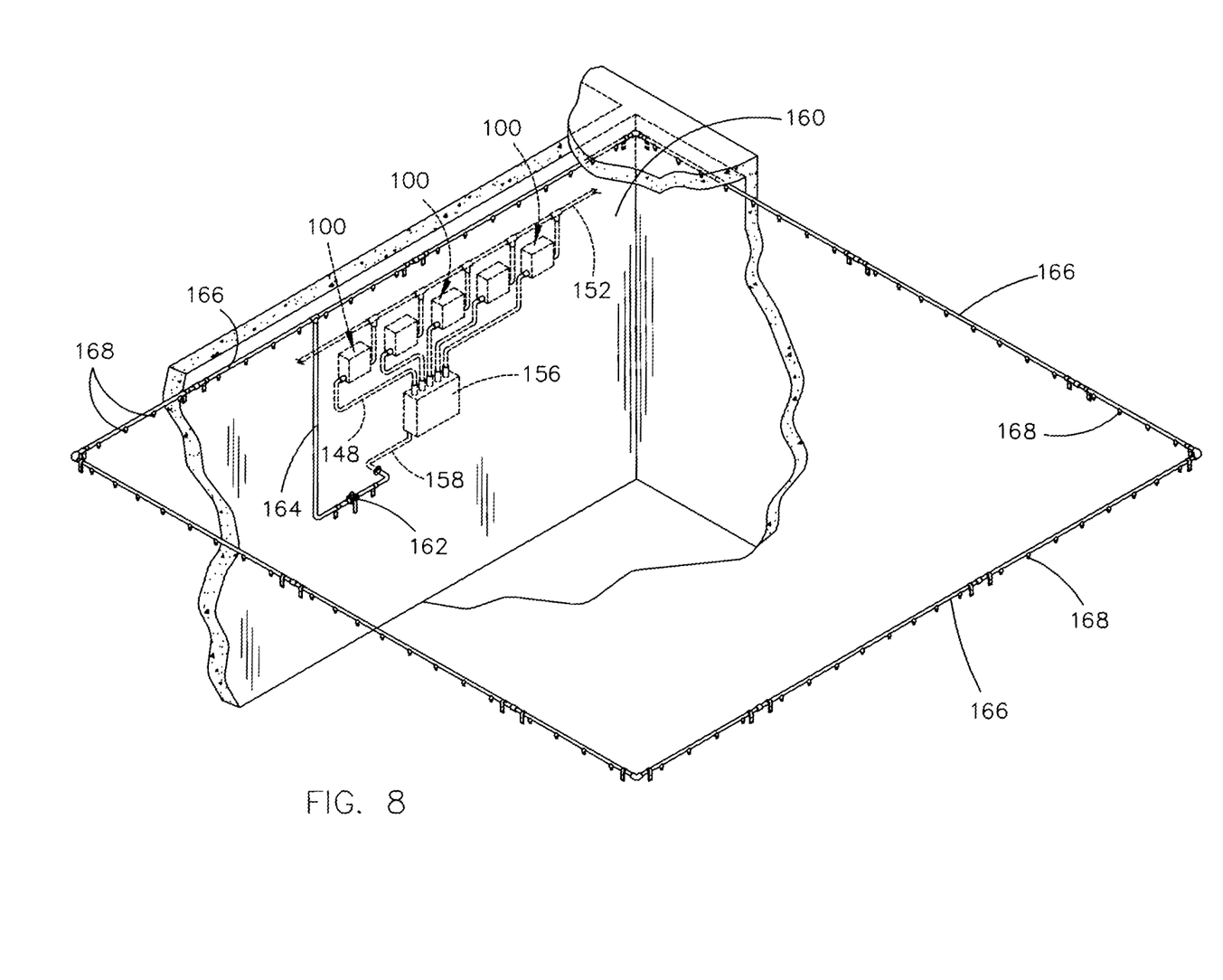
FIG. 8 is a partial perspective view illustrating the systems of this invention being connected to a wall washing system.
Figure 9:
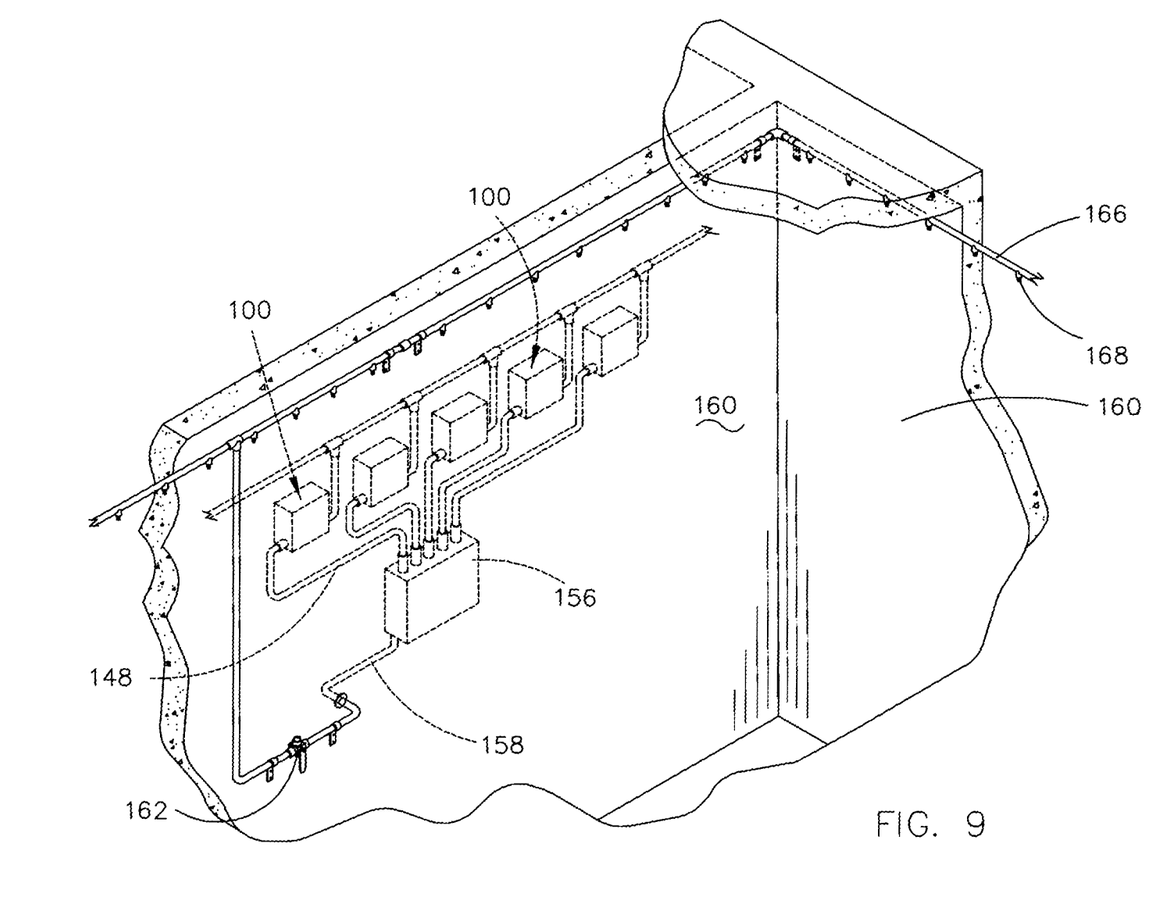
FIG. 9 is a similar, but enlarged, partial view of FIG. 8.
Figure 10:
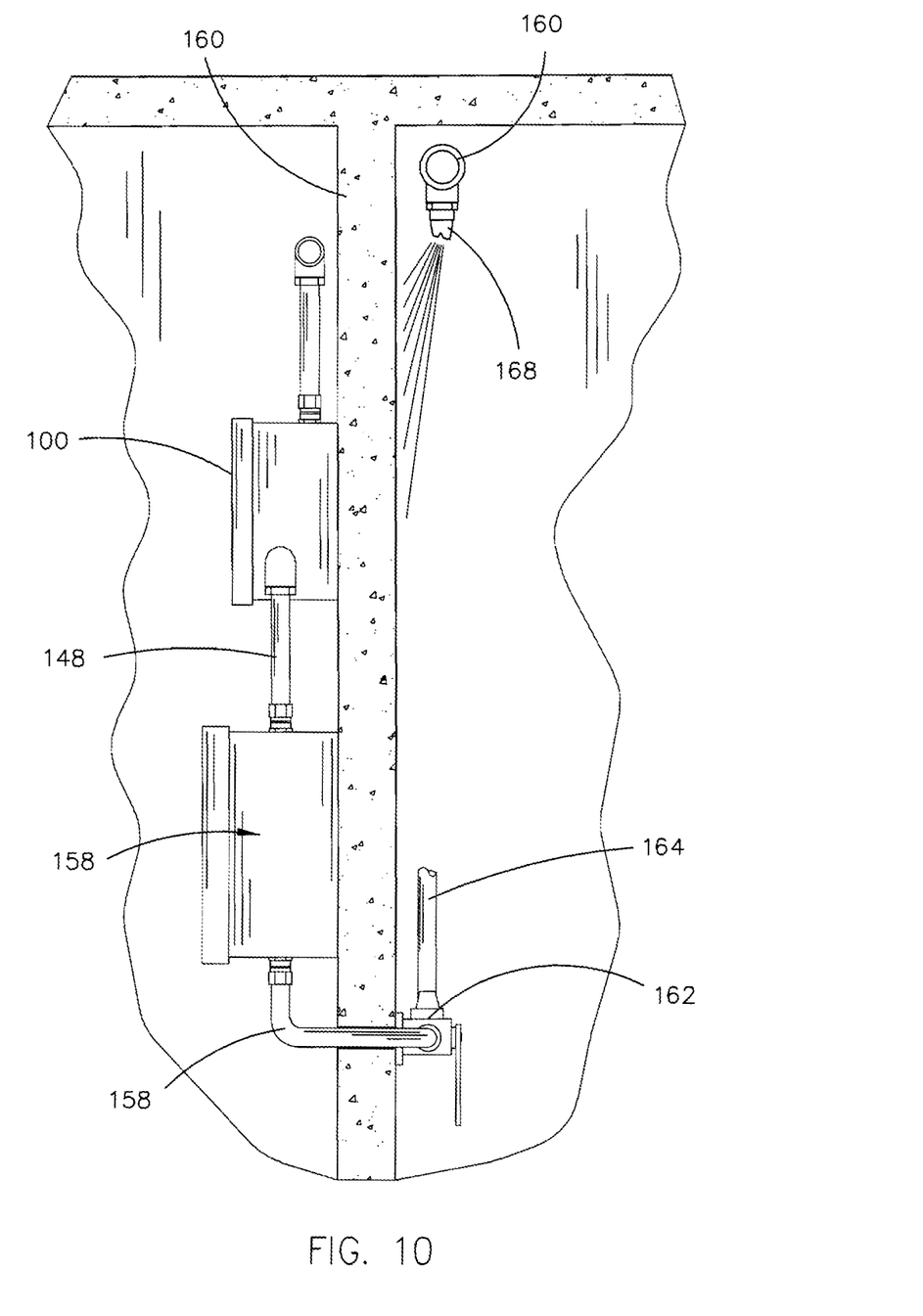
FIG. 10 is a partial sectional view illustrating the manner in which the walls of an enclosure are washed.

Microbiological organisms/species can reside in water sources, including water intended for drinking recreation. Among the microbiological threats is the protozoan parasite—*cryptosporidium* (crypto). Crypto can be a particular challenge for the water treatment industry, however, ozone can eliminate it. Ozone, molecularly known as $O_3$, is a sanitizer and is relentless in its attack of organic microbes (bacteria, viruses, cysts, etc). Through a process known as lysing, ozone breaks down cell walls or membranes, where it can then destroy the nucleus of the microbe. In addition to sanitation, ozone can provide for the oxidizing of inorganic material that could be present in water, such as metals (e.g., iron and manganese). Although there are a few stronger oxidizers, ozone is the strongest that is readily available for commercial or residential use. FIG. 6 provides a chart showing relative oxidizer strength for a variety of oxidizers. As shown, ozone is about 1.5 times stronger than chlorine, and can provide a faster oxidizing action. Furthermore, because of this higher oxidation strength, ozone does build up a tolerance to microbes unlike other sanitizers, such as chlorine. Within the microbial world protozoa, such as crypto, are some of the most resistant to all types of disinfectants. One reason for this resistance is due to its hard outer protective shell, which must be broken through prior to the microbe being inactivated. Crypto can cause a variety of ailments, including abdominal cramping, diarrhea, fever and nausea that can last as long as a month, according to the Centers for Disease Control and Prevention (CDC). Disinfectants used to ward off *cryptosporidium* for water treatment applications can include chlorine (liquid state), chloramines, chlorine-dioxide (gaseous state), and ozone. However, their ability to perform this inactivation duty should not be regarded equal, as each sanitizer requires a specific level of concentration and contact time to take effect, as described by the following.

To better determine the specific amount of the disinfectant required to inactivate or destroy a microbe, the Environmental Protection Agency (EPA) has determined Ct Values. These Ct Values are the product of the disinfectant's concentration (C, expressed in mg/L) and the contact time (t, expressed in minutes). These Ct Values are calculated specifically to the percentage of microbial kill or better known as the log reduction, e.g. 1-Log=90.0 percent, 2-Log=99.0 percent or 3-Log=99.9 percent inactivation of the particular microbe. According to the EPA, chlorine dioxide would require a Ct of 226, which would correlate to 226 mg/L, at one minute of contact time, at 25° C. to achieve a 3-Log reduction or 99.9 percent inactivation. Although, ozone would only require a Ct of 7.4, correlating to 7.4 mg/L, to achieve the same 99.9 percent inactivation with the same parameters as chlorine dioxide. Ct is a product of concentration and time, and as such, both can be manipulated, as long as the given Ct Value is obtained for the desired log reduction (e.g. Ozone Ct of 7.4 can be achieved with a concentration 3.7 mg/L for two minutes of time).

*Cryptosporidium* outbreaks in public drinking waters and recreational swimming pools are becoming more and more of an evident issue. Unfortunately, forms of chlorine sanitation are not often the best solution, especially for high organic and inorganic contaminant levels, as they will create chlorine oxidation by-products, such as trihalomethanes (THM) and chloramine derivatives. These by-products are the typical cause of (what most associate as being over chlorinated) the chlorine smell in drinking or pool waters, and are the cause of itchy, smelly skin and burning eyes in pool water. Although with a properly sized system, ozone can be used as the primary sanitizing and oxidizing agent, oxidizing the contaminants completely. Using ozone in this manner would then allow chlorine to be used as the secondary residual sanitizer to satisfy regulatory requirements, without the production of chloramines and chlorine's side effects.

Further, ozone can be used to remove iron and manganese from water, forming a precipitate that can be filtered:

$$2Fe^{2+}+O_3+5H_2O \rightarrow 2Fe(OH)_3(s)+O_2+4H^+$$

$$2Mn^{2+}+2O_3+4H_2O \rightarrow 2MN(OH)_2(s)+2O_2+4H^+$$

Ozone will also reduce dissolved hydrogen sulfide in water to sulfurous acid:

$$3O_3+H_2S \rightarrow 3H_2SO_3+3O_2$$

The reactions involved iron, manganese, and hydrogen sulfide can be especially important in the use of ozone-based well water treatment. Further, ozone will also detoxify cyanides by converting the cyanides to cyanates (on the order of 1,000 times less toxic):

$$CN^-+O_3 \rightarrow CNO^-+O_2$$

Ozone will also completely decompose urea, where recent outbreaks of *E. coli* in lettuce have been impacted by urea:

$$(NH_2)_2CO+O_3 \rightarrow N_2+CO_2+2H_2O$$

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A pathogenic control system, comprising:
   a plurality of spaced-apart housings;
   each of said housings comprising:
   (a) an ozone generator, having an inlet port and an outlet port, configured to generate ozone;
   (b) a water inlet configured to receive water from a water source;
   (c) a venturi, having an inlet port and an outlet port, coupled with the water source to receive water within the venturi, said venturi also being coupled with said ozone generator and configured to introduce ozone generated by said ozone generator to water received at said water inlet to provide a water and ozone solution having an ORP of at least 600 millivolts;
   (d) a water outlet coupled with said outlet port of said venturi, said water outlet having a fluid pressure of the water and ozone solution less than the fluid pressure of water received at said water inlet;

a pump having an intake side and a discharge side;

each of said water outlets of said housings being in fluid communication with said intake side of said pump;

said water outlets which are coupled to said Venturis being fluidly connected to said intake side of said pump in a parallel manner;

a wall washing apparatus spaced from said housings with the wall washing apparatus including an elongated and horizontally disposed spray pipe positioned at the upper end of the wall to be washed;

said spray pipe having a fluid intake end which is fluidly connected to said discharge side of said pump;

said spray pipe having a plurality of spaced-apart spray nozzles mounted therein;

said spray nozzles discharging the water and ozone solutions produced by said system onto the upper end of the wall to be washed so that the water and ozone solution will flow downwardly on the wall to cleanse and disinfect the same.

2. The system of claim 1, further comprising:

a cover portion coupled with each of the housings to enclose at least the ozone generator and the venturi within an interior portion of the housing when the cover portion is secured to the housing.

3. The system of claim 1, further comprising:

an in-line mixer coupled between the venturi and the water outlet, the inline mixer configured to provide contact time between the ozone and the water during a vortex generated by the venturi.

4. The system of claim 3, wherein said in-line mixer has an internal diameter that is the same as the internal diameter of said outlet port of the venturi to which said in-line mixer is coupled.

5. The system of claim 1, wherein said ozone generator includes a corona discharge tube.

6. The system of claim 1, further comprising:

a compressor coupled to said input port of said ozone generator, said compressor being configured to receive ambient air and apply a pressure to the ambient air; and a filter positioned to filter the received ambient air.

7. The system of claim 6, wherein said filter is configured to absorb at least a portion of water vapor from the received ambient air.

8. The system of claim 6, wherein said compressor is configured to apply a pressure to the received ambient air of at least 15 KPa.

9. The system of claim 1, wherein the water and ozone solution has a molar concentration of ozone of at least twenty percent.

10. The system of claim 1, further comprising:

a flow meter coupled between the water inlet and the water outlet, said flow meter positioned to detect a flow of water received from the water source.

11. The system of claim 10, further comprising:

an indicator coupled with said flow meter, said indicator configured to receive a signal upon detection by said flow meter of the flow of water and provide an indication in response thereto.

12. The system of claim 11, wherein said indicator includes an illuminated light source.

13. The system of claim 11, further comprising:

a power source coupled with each of said ozone generators to provide power to generate the ozone; and a relay coupled to each of the power source, said flow meter, and said indicator, said relay configured to provide an activation signal to said indicator upon receipt of a signal from each of the power source and said flow meter.

14. The system of claim 1, wherein the water and ozone solution has an ORP of at least 650 millivolts.

15. The system of claim 1 wherein a plurality of spray pipes are positioned on a plurality of the walls to be washed.

* * * * *